United States Patent [19]
Hill et al.

[11] Patent Number: 5,538,864
[45] Date of Patent: Jul. 23, 1996

[54] BACTERIOPHAGE RESISTANT RECOMBINANT BACTERIA

[75] Inventors: Colin J. Hill, Cork, Ireland; Todd R. Klaenhammer, Raleigh, N.C.

[73] Assignee: North Carolina State University, Raleigh, N.C.

[21] Appl. No.: 373,877

[22] Filed: Jan. 17, 1995

Related U.S. Application Data

[63] Continuation of Ser. No. 21,176, Feb. 19, 1993, abandoned, which is a continuation of Ser. No. 577,954, Sep. 5, 1990, abandoned.

[51] Int. Cl.⁶ .................... C12N 1/20; A23C 9/00; C12P 7/56
[52] U.S. Cl. .................... 435/69.1; 426/61; 435/139; 435/235.1; 435/236; 435/243; 435/252.3
[58] Field of Search .................... 435/69.1, 139, 435/172.1, 172.3, 243, 320.1, 235.1, 252.3, 252.4, 236; 426/42, 61; 536/23.1, 24.1

[56] References Cited

U.S. PATENT DOCUMENTS

| | | | |
|---|---|---|---|
| 4,732,859 | 10/1989 | Hershberger et al. | 435/320.1 |
| 4,874,616 | 10/1989 | Vedamuthu | 426/43 |
| 4,883,756 | 11/1989 | Klaenhammer et al. | 435/252.3 |
| 4,918,014 | 4/1990 | Vedamuthu | 435/172.1 |
| 4,931,396 | 6/1990 | Klaenhammer et al. | 435/252.3 |

OTHER PUBLICATIONS

Backman et al., Science, 196: 182–183 (1977).
Sanders, Brochimie, 70: 411–421 (1988).
Geider et al., Gene 33: 341–349 (1985).
Jarvis, Appl. Environ. Microbiol., 47(2): 343–349 (1984).
Dao et al., Appl. Environ. Microbiol., 49(1) 115–119 (1985).
Levin et al., FEBS Lett., 222(1): 199–203 (1987).
Zipser et al., Gene 2: 263–271 (1977).
C. Hill et al., *Applied and Environmental Microbiology* 57, No. 1, 283–288 (1991).
C. Hill et al., *Journal of Bacteriology* 172, No. 11, 6419–6426 (1990).
T. Klaenhammer, *Advances in Applied Microbiology* 30, 2–29 (1984).
Zagursky and Berman, "Cloning vectors that yield high levels of single–stranded DNA for rapid DNA sequencing", Gene 27: 183–191, 1984.
Dotto et al., "Functional analysis of bacteriophage f1 intergenic region", Virology 114: 463–473, 1981.
Cleary and Ray, "Replication of the plasmid pBR322 under the control of a cloned replication origin from the single–stranded DNA phage M13", Proc. Nat. Acad. Sci USA 77: 4638–4642, 1980.

*Primary Examiner*—Mindy B. Fleisher
*Assistant Examiner*—Bonnie D. Weiss
*Attorney, Agent, or Firm*—Bell, Seltzer, Park & Gibson

[57] ABSTRACT

Recombinant bacteria containing phage-encoded resistance ("Per") and methods of making and using the same are disclosed. Such bacteria are made by (a) conducting a fermentation of a substrate in a medium containing a defined bacterial culture until bacteriophage are detected in the medium, the bacteriophage being specific to at least one bacteria in the medium; (b) isolating the bacteriophage; (c) digesting DNA of the bacteriophage to produce a library of DNA fragments; (d) transforming the bacteria susceptible to said bacteriophage with the library of DNA fragments to provide transformed bacteria; (e) selecting from among the transformed bacteria, a bacteriophage-resistant transformed bacteria; (f) adding bacteriophage resistant transformed bacteria to the medium; and (g) recommencing step (a). Also disclosed are bacterial cells which contain a first bacteriophage defense mechanism (Per), wherein Per comprises a bacteriophage origin of replication (ori) operatively associated with a DNA sequence incapable of producing live bacteriophage. The bacterial cell is capable of being infected by a bacteriophage, the DNA of which, once injected into the bacterial cell, competes with Per for binding to DNA polymerase.

13 Claims, 5 Drawing Sheets

```
   1  CAGTGCCAAGCTTGCATGCCTGCAGGTCGACGCTATCGATAAGCTTCAAATAATGCCATT
  61  TCTCGAGGATTCATGCAAGGTAAAGCTTTGCAAGCCTGGTCAATGTTCTCTGGTGGTGAA
                        MetGlnGlyLysAlaLeuGlnAlaTrpSerMetPheSerGlyGlyGlu
 121  ATGGCTCTGGCAACAGAGCAAGGTGATATTCAAGGAGAATCAACTGAACGCATTTTAAAG
      MetAlaLeuAlaThrGluLysThrHisValAlaArgAlaIleGlyGlnAsnGlnSerPheVal
 181  ATTATCGCAACTGAAAAAACTCACGTTGCTCGAGCGATTGGTCAAAATCAATCGTTTGTT
      IleIleAlaThrGluLysThrHisValAlaArgAlaIleGlyGlnAsnGlnSerPheVal
 241  AATCTGACCAGTGTGTTATGCGTTGATACAAATCGAACTGTTGCGCTCTCTGATGAAATG
      AsnLeuThrSerValLeuCysValAspThrAsnArgThrValAlaLeuSerAspGluMet
 301  GACGGCCGAAAAGTGTTAATTCAATTTAAAGATCGTCCTAAAAATGAAACAGATATTCAA
      AspGlyArgLysValLeuIleGlnPheLysAspArgProLysAsnGluThrAspIleGln
 361  CGAGAGCGGATTTTCAAAAAATATTGGGATACTTTTACAACAAAAGATAAAATTCCAGAT
      ArgGluArgIlePheLysLysTyrTrpAspThrPheThrThrLysAspLysIleProAsp
 421  ATTTCAGGATGTATAGGTTTCTTACTAAATTCGTTGGATTACTTTAACGAACTTGCGAAA
      IleSerGlyCysIleGlyPheLeuLeuAsnSerLeuAspTyrPheAsnGluLeuAlaLys
 481  ATGTACATTTGGAAAAATGTTGAAGTGTTCAATGATATTGATTTAGATGATTTTCAAACT
      MetTyrIleTrpLysAsnValGluValPheAsnAspIleAspLeuAspAspPheGlnThr
 541  GCTTTGATTAACGCTTTGCAAGAAATTGAATTTGTACAACGTACAGATAACGAAGAAGTT
      AlaLeuIleAsnAlaLeuGlnGluIleGluPheValGlnArgThrAspAsnGluGluVal
 601  ATTGCTTTATCTAATCAAGTCTATGGTAAAAATATGAACGCTCTAAATAAATCTTTATCA
      IleAlaLeuSerAsnGlnValTyrGlyLysAsnMetAsnAlaLeuAsnLysSerLeuSer
 661  GAAATAGGAGTTGAAGCTATTTCTAAAAAGATTAACGCGAAAAAAGTTAGAGGGTATTCT
      GluIleGlyValGluAlaIleSerLysLysIleAsnAlaLysLysValArgGlyTyrSer
 721  ATATCTAATAAAGATAGATTTAATAAAGATAGATTTAATAAATTCATTGATGAATAGAGG
      IleSerAsnLysAspArgPheAsnLysAspArgPheAsnLysPheIleAspGlu
 781  TACCGAGGGTACCGAGGTGGTACCGAGGTTTTTTGTAAAGCTCGGTACCGCTAAAACGTC
 841  AATAACCACAAGGGTTTTCAGCATAAAAATAATAAAGGTACCGAGGTTCTTACCATATAT
 901  CAAAGACTAATTAAATGTTTAAGATATATATTATATAAGGGTGGGGTACCTAAGACCTCG
 961  GTACCCTTGGTACCGAATAGTCTGAAACCTTATAAAATATGGCTTCGTGGAGGTTGTGCG
1021  GTTGTACCGAGGTTTCCGATGTAGTACCGAGGGTTCCGAGGTGGTACCGAGGTTTTTTGT
1081  AAAGCTCGGTACCGCTAAAACGTCAATAATCACAAGGGTTTTCAGCATAAAAATAATAAA
1141  GGTACCGAGGTTCTTACCATATATCAAAGACTAATTAAATGTTTAAGATATATATTATAT
1201  AAGGGTGGGGTACCTAAGACCTCGGTACCCTCGGTACCGAATAGTCTGAAACCTTATAAA
1261  ATATGGCTTCGTGGAGGTTCCGAGGTGAGCAAAACAGCACTCTCATTTTTATCAAAAGGC
1321  TATCAAGTCATTCCGTTGAACAGAAAAACTGGCACACCTATCACTAAATTTAAAGACATT
1381  CCAGTTACTGAAGAATTTATTAACAGTTTGAATTGGGATAATTGCGATGGG   1431
```

FIG. 3.

```
                T
          T     G
        T       T
       T: :A
       T: :A
       T: :A
        G  G
       G: :C
       A: :T
       G: :C         FREE
       C: :G         ENERGY
       C: :G       -18.3 kCal
       A: :T
       T: :A
       G: :C              FIG. 4A.
       G: :C
        T  G
 792   G: :C    836
 CCGAG         TAAAA
 1056           1100
```

```
              C  G
            T      G
           C        T
           C        A
            A      C
             G: :C
             A  C          FREE
             A: :T        ENERGY
             T  T/C       -11 kCal
             C: :G
             C: :G
  FIG. 4B.   A: :T
             T: :A
             G: :C
      939   G: :C    980
     GGGIGG        GAATAG
      1203           1244
```

BACTERIOPHAGE RESISTANT RECOMBINANT BACTERIA

This is a continuation of application Ser. No. 08/021,176, filed on Feb. 19, 1993, abandoned, which is a file wrapper continuation of application Ser. No. 07/577,954, filed on Sep. 5, 1990, now abandoned.

FIELD OF THE INVENTION

The present invention relates to bacteriophage resistant recombinant bacteria and their use in fermentation.

BACKGROUND OF THE INVENTION

Production of cheese and cultured dairy products has long relied on the fermentation of milk by lactic acid-producing bacteria including species of Lactococcus. Since efficient fermentations are dependent on the growth and activity of these bacteria, great care is exercised to prepare starter cultures that are highly active and uncontaminated with undesirable microorganisms or bacteriophages. However, the fermentation process itself is nonaseptic, occurring in open vats with a nonsterile medium, e.g., pasteurized milk. It is, therefore, highly susceptible to contamination with bacteriophages. For the majority of strains of lactic acid bacteria employed in commercial dairy fermentations, lytic bacteriophages capable of halting growth and acid production can appear within one to two days after introducing the bacterial culture into the dairy plant.

Milk fermentations historically have relied on starter cultures composed of undefined mixtures of lactic acid bacteria propagated without knowledge of, or protection from, bacteriophages. Natural bacteriophage contamination in these cultures established an equilibrium of evolving bacteriophages and bacteriophage-resistant variants. These cultures were highly variable in day-to-day levels of acid production, but remained moderately active and could be used continuously in small fermentation factories. Over the past 20 years, starter culture failures due to bacteriophage infection have become prevalent throughout the dairy industry. Increasing demand for cultured milk products in recent years has necessitated increases in both production capacity and process efficiency such that larger volumes of milk are processed, cheese vats are filled repeatedly within a single day, and total processing time is shortened. This modernization of the industry concurrently increased the probability of bacteriophage contamination and further dictated the use of defined mixtures of lactic acid bacteria capable of uniform and rapid rates of acid production. With the selection of highly fermentative lactic acid bacteria and their propagation under aseptic conditions, i.e., in the absence of bacteriophages, the majority of cultures now used by the industry are susceptible to bacteriophage attack upon introduction into the cheese factory.

To cope with bacteriophage problems, a number of methods have been developed to minimize bacteriophage action during various fermentation processes, particularly dairy fermentations.

Bacteriophage resistance in various lactic acid bacteria is recognized generally as a plasmid-encoded phenomenon. For example, U.S. Pat. No. 4,732,859 to Hershberger et al. relates to a method of protecting various genera of bacteria from naturally occurring bacteriophage by providing host bacterial cells with a restriction system that digests HhaII site-containing foreign DNA, found in most naturally occurring phages. As bacteriophage DNA enters a host cell, the HhaII restriction endonuclease digests the DNA at HhaII sites and renders the bacteriophage non-functional and harmless. In more general terms, the invention involves transforming a bacterium with a recombinant DNA cloning vector which comprises a replicon that is functional in the bacterium, and a gene that expresses a functional protein (i.e., a restriction endonuclease which confers restriction activity to the bacterium).

U.S. Pat. Nos. 4,918,014 and 4,874,616, both to Vedamuthu, are directed to a method of imparting bacteriophage resistance to bacteriophage sensitive strands of Streptococcus group N, whereby a plasmid encoding the production of a mucoid substance is transferred via a plasmid into a bacteriophage sensitive strain. The lactic Streptococci, or "Lactococci," are said to be rendered bacteriophage resistant, and purportedly more stable for use in milk fermentation.

Bacteriophage resistance in Lactococci also has been found generally to be a plasmid-encoded phenomenon. Plasmids have been described which direct resistance via inhibition of adsorption, restriction and modification ("R/M"), and by aborting the bacteriophage infection ("Hsp"). Strategies that will be useful for the construction of bacteriophage-insensitive strains include the introduction of one or more resistance mechanisms within a single host, or introducing a single plasmid containing more than one resistance mechanism. For recent reviews, see Klaenhammer, T. R., *FEMS Microbiol.* Rev. 46:313–325 (1987) and Sanders, Biochimie 70:411–422 (1988). A prerequisite for the success of these strategies is that the resistance mechanisms should work in combination to prevent bacteriophage proliferation. The insensitivity of any constructed, or natural, isolate is probably a function of time, amount of use, and environmental conditions (Klaenhammer, 1984, Lawrence and Thomas, 1979). The presence of single plasmids encoding multiple resistances, or combinations of plasmids within a single strain, can also confer prolonged resistance phenotypes upon lactococcal strains. Inevitably, however, defense mechanisms used for long periods have succumbed to an evolving bacteriophage population. This has occurred, for example, in the case of pTR2030 transconjugants of the industrial strain of L. lactis, NCK202. pTR2030 is a conjugative plasmid which confers resistance to bacteriophage via Hsp and R/M. Bacteriophages recovered from the industry after prolonged use of NCK202 have overcome either one or both of these mechanisms.

The search for novel resistance determinants to add to the growing arsenal of available, independent genotypes has continued. In particular, bacteriophage defense mechanisms active against those that are insensitive to Hsp would provide a valuable adjunct to existing resistance genotypes in bacteria, particularly lactic acid bacteria. Most avenues of bacteriophage replication could be blocked to minimize the adaptation and proliferation of new bacteriophages, which in turn would increase the longevity of fermentation bacterial cultures.

SUMMARY OF THE INVENTION

In accordance with the above, the present inventors have identified a heretofore unknown resistance mechanism of bacteria to bacteriophage, termed Phage encoded resistance, or "Per." Per is unique among bacterial genotypes since it is derived from the genome of the bacteriophage itself.

More specifically, a first aspect of the present invention comprises:

(a) conducing a fermentation of a substrate in a medium containing a defined bacterial culture until bacteriophage are detected in the medium, the bacteriophage being specific to at least one bacteria in the medium;

(b) isolating the bacteriophage;

(c) digesting DNA of the bacteriophage to produce a library of DNA fragments;

(d) transforming the bacteria susceptible to said bacteriophage with the library of DNA fragments to provide transformed bacteria;

(e) selecting from among the transformed bacteria, a bacteriophage-resistant transformed bacteria;

(f) adding bacteriophage resistant transformed bacteria to the medium; and (g) recommencing step (a).

A second aspect of the present invention comprises a bacterial cell which contains a first bacteriophage defense mechanism (Per), wherein Per comprises a bacteriophage origin of replication (ori) operatively associated with a DNA sequence incapable of producing live bacteriophage. The bacterial cell is capable of being infected by a bacteriophage, the DNA of which, once injected into the bacterial cell, competes with Per for binding to DNA polymerase.

A third aspect of the present invention comprises a defined bacterial starter culture capable of fermenting a product, comprising a plurality of bacterial cells which contain a first bacteriophage defense mechanism (Per). Per comprises a bacteriophage origin of replication (ori) operatively associated with a DNA sequence incapable of producing live bacteriophage. The bacterial cells are capable of being infected by a bacteriophage, the DNA of which, once injected into the bacterial cell, competes with Per for binding to DNA polymerase.

A fourth aspect of the present invention comprises a method of conducting a fermentation of a product, which comprises providing to a fermentation medium, a defined bacterial starter culture comprising a plurality of bacterial cells which contain a first bacteriophage defense mechanism (Per) comprising a bacteriophage origin of replication (ori) operatively associated with a DNA sequence incapable of producing live bacteriophage, wherein the DNA of the bacteriophage, once injected into the bacterial cell, competes with Per for binding to DNA polymerase.

A fifth aspect of the present invention involves a recombinant DNA vector comprising a bacteriophage origin of replication (ori) operatively associated with a DNA sequence incapable of producing live bacteriophage.

These aspects are more completely described hereinbelow. In addition, other aspects of the present invention not explicitly set forth herein will become apparent to those skilled in the art.

BRIEF DESCRIPTION OF THE DRAWINGS

In FIG. 1B, the shaded box represents the 4.5-kb BamH1—HindIII bacteriophage fragment cloned in pTRK103 (Per+).

FIG. 3 shows the nucleotide sequence of the pTRK104 insert and deduced amino acid sequence of the open reading frame (ORF). The 236-bp direct repeat is indicated by the bold arrows. The 10-bp direct repeats are indicated by the thin arrows. The positions of both HindIII sites are overlined. M13 flanking sequences are boxed. These sequences have been deposited in GenBank under accession number M35639.

DETAILED DESCRIPTION OF THE INVENTION

Many bacteriophage genomes contain a unique origin of replication, hereinafter generically referred to as "ori." These regions typically contain special features such as binding sites for specific initiator proteins and adjacent stretches of AT-rich regions which presumably aid in the unwinding of DNA. See *The Bacteriophages*, (R. Calendar Ed. 1988) (Plenum Press), Volume 2 Chapter 3, pp. 146 et seq. The duplication of bacteriophage DNA begins at ori primed by RNA. The RNA primer is synthesized by either a host- or a bacteriophage-coded RNA polymerase or a primase enzyme, and is elongated into DNA by a host- or bacteriophage-coded DNA polymerase. Id. While the present inventors do not wish to be bound to any specific theory upon which the instantly disclosed invention operates, it appears that the presence of a given bacteriophage ori on a multi-copy factor such as a plasmid contained in a bacterial cell interferes with the normal lytic process by titrating DNA polymerase and diverting bacteriophage replication towards the plasmid. In other words, ori presents a false target for DNA polymerase, which results in the uncontrolled replication of the plasmid DNA.

In accordance with the foregoing, a method for imparting bacteriophage resistance to fermentative bacteria capable of being infected by a bacteriophage has been devised. The first step in the method involves commencing a fermentation of a substrate in a medium containing a defined bacteria culture, and continuing fermentation until bacteriophage specific to at least one bacterial species in the medium are detected. By the term "specific," it is meant that the bacteriophage are capable of infecting the bacterial species, that is, the process whereby bacteriophage bind to the outer cell membrane of the bacterial cell and inject their genetic material into the bacteria, whereafter the bacteriophage genetic material duplicates, progeny bacteriophage produced, the bacterial cell lysed and the progeny bacteriophage released into the medium. Other bacterial cells are then infected by the progeny bacteriophage. Once the bacteriophage has been identified, it is isolated, and the genetic material, i.e., DNA, of the bacteriophage is digested and a library of DNA fragments is produced. The production of a DNA library using the genetic material of a given microorganism is a known technique, and is well documented in the prior art. See generally T. Maniatis et al., *Molecular Cloning: A Laboratory Manual* (Cold Spring Harbor Laboratory 1982). Thereafter, the bacteria susceptible to the phage are transformed with the library of DNA fragments, also in accordance with known techniques supra, to provide recombinant bacteria.

When the library of DNA fragments is made, they must be joined to heterologous DNA which is incapable of coding for the phage from which the fragments are derived. In a preferred embodiment of the present invention, the DNA library is made by first inserting the fragments of the library into a plasmid vector, transforming the bacteria susceptible to the bacteriophage with the plasmid vector, and then propagating the transformed bacteria. However, other ways of cloning the DNA library are known in the art and will become apparent to those skilled therein without undue experimentation. For example, the library can be constructed in any host, such as *E. coli* or Bacillus, and transferred to the susceptible bacteria with an appropriate shuttle vector.

Bacteriophage resistant bacteria are selected from among the transformed bacteria by standard screening procedures, and then added to the fermentation medium. Fermentation is recommenced and continued until other bacteriophage specific to a given bacterial species are detected. This might occur, for example, if the culture medium contained two or more bacterial species, i.e., a mixed culture.

The art of fermentation is well known and the instant method is operable in a wide variety of fermentation processes. In a preferred embodiment according to the present invention, the instant method relates to bacteria capable of fermenting food substrates, and more particularly milk.

Bacteria capable of fermenting foods include those bacteria used in any type of food fermentation, including, but not limited to, the fermentation of milk, egg, meat, fruit, vegetables, and cereals. See generally Food Biotechnology, (D. Knorr Ed. 1987)(Marcel Dekker, Inc.); Fermented Foods (A. Rose Ed. 1982)(Academic Press); C. Pederson, Microbiology of Fermented Foods, (2d ed. 1979)(AVI Publishing Co.).

Bacteria used for the fermentation of meat (including beef, pork, and poultry) include, but are not limited to, lactic acid bacteria, *Pediococcus cerevisiae, Lactobacillus plantarum, Lactobacillus brevis, Micrococcus species, Leuconostoc citrovorum, Leuconostoc citrovorum*, and mixtures thereof. See Food Biotechnology, 538–39 (D. Knorr Ed. 1987); C. Pederson, Microbiology of Fermented Foods, 210–34 (2d ed. 1979); U.S. Pat. No. 2,225,783 to Jensen and Paddock.

Bacteria used for the fermentation of vegetables (e.g., carrots, cucumbers, tomatoes, peppers, and cabbage) include, but are not limited to, *Lactobacillus plantatum, Lactobacillus brevis, Leuconostoc mesenteroides, Pediococcus pentosaceus*, and mixtures thereof. See Food Biotechnology, 540 (D. Knorr Ed. 1987); C. Pederson, Microbiology of Fermented Foods, 153–209 (2d ed. 1979); U.S. Pat. No. 3,024,116 to Engelland; U.S. Pat. No. 3,403,032 to Etchells et al.; U.S. Pat. No. 3,932,674 to Etchells et al.; U.S. Pat. No. 3,897,307 to Porubcan et al.

Bacteria used in the fermentation of dough formed from cereals (e.g., wheat, rye, rice, oats, barley, and corn) include yeasts such as *Saccharomyces cerevisiae* and *Candida utilis;* and lactic acid bacteria of the genera Lactobacillus, Lactococcus, Pediococcus and Leuconostoc, including, but not limited to *Lactobacillus delbrueckii, Lactobacillus debreuckii* subsp. *leichmanni, Lactobacillus plantarum, Lactobacillus casei, Lactobacillus brevis, Lactobacillus fermenti, Lactobacillus pastorianus, Lactobacillus buchneri*, and *Leuconostoc mesenteroides*. See generally Food Biotechnology, 235–70 (D. Knorr Ed. 1987); U.S. Pat. No. 3,734,743 to Kline and Sugihara; U.S. Pat. No. 3,681,083 to Everson; U.S. Pat. No. 3,993,783 to Khoudokormoff and Langejan; U.S. Pat. No. 3,843,800 to Langejan; U.S. Pat. No. 3,410,692 to Wutzel.

Wine is produced by the fermentation of fruit juice, typically grape juice, with yeasts, such as *Saccharomyces cerevisiae* and *Saccharomyces ellipsoideus*, as well as with a broad variety of lactic acid bacteria including *Pediococcus pentosaceus, Lactobacillus plantarum, Leuconostoc mesenteroides, Leuconostoc dextranicum, Leuconostoc cremoris, Lactobacillus brevis*, and *Lactobacillus fermenti*. Beer is produced by the fermentation of malt with yeasts such as *Saccharomyces cerevisiae* and *Saccharomyces carlsbergensis*. See C. Pederson, Microbiology of Fermented Foods, 271–309 (2d ed. 1979).

Milk is fermented to produce products such as cheese, yoghurt, kefir, and acidophilus milk. Cheese fermentation bacteria are discussed separately below. Otherwise, bacteria used for the fermentation of milk include, but are not limited to, *Lactobacillus debreuckii* subsp. *bulgaricus, Lactobacillus acidophilus, Streptococcus salivarius* subsp. *thermophilus*, and mixtures thereof. See Food Biotechnology, 530 (D. Knorr Ed. 1987); C. Pederson, Microbiology of Fermented Foods, 105–35 (2d ed. 1979).

Bacteria used for the fermentation of milk to produce cheese include, but are not limited to, *Lactobacillus bulgaricus, Lactobacillus helveticus, Streptococcus salivarius* subsp. *thermophilus, Lactococcus lactis* subsp. *lactis, Lactococcus lactis* subsp. *cremoris, Lactococcus lactis* subsp. *lactis biovar. diacetylactis*, and mixtures thereof. See Food Biotechnology, 530 (D. Knorr Ed. 1987); C. Pederson, Microbiology of Fermented Foods, 135–51 (2d ed. 1979).

Bacteria used for the fermentation of egg include *Pediococcus pentosaceus, Lactobacillus plantarum*, and mixtures thereof. See Food Biotechnology, 538–39 (D. Knorr Ed. 1987).

In a particularly preferred embodiment, the present invention is employed for the fermentation of milk with the lactococci (previously classified as the group N Streptococci), such as *Lactococcus lactis* subsp. *lactis*, (also called *Lactococcus lactis*), *Lactococcus lactis* subsp. cremoris (also called *Lactococcus cremoris*), and *Lactococcus lactis* subsp. *lactis biovar. diacetylactis* (also called *Lactococcus diacetylactis*).

Starter cultures employed in practicing the present invention may be in any physical form, including liquid cultures of the fermentation bacteria in a suitable growth medium, as well as lyophilized cultures and frozen cultures prepared therefrom.

Starter cultures employed in the present invention are preferably defined cultures, that is, cultures of known bacterial content. Such defined cultures may be either single strain cultures, i.e., pure cultures, or multiple strain cultures, i.e., mixed cultures.

While the present invention is, in a preferred embodiment, directed to the fermentation of food, the invention may be practiced with any process involving fermentative bacteria susceptible to disruption by bacteriophage infection, including but not limited to processes for the production of antibiotics, amino acids, and solvents. Products produced by fermentation which are known to have encountered bacteriophage infection, and the corresponding infected fermentation bacteria, include Cheddar and cottage cheese (*Lactococcus lactis, Lactococcus cremoris), Yogurt (Lactobacillus bulgaricus, Streptococcus thermophilus), Swiss cheese (S. thermophilus, Lactobacillus lactis, Lactobacillus helveticus), Blue cheese (Leuconostoc cremoris), Italian cheese (L. bulgaricus, S. thermophilus), Viili (Lactococcus cremoris, Lactococcus lactis subsp. diacetylactis, Leuconostoc cremoris), Yakult (lactobacillus casei), casein (Lactococcus cremoris), Natto (Bacillus subtilis var. natto), Wine (Leuconostoc oenos), Sake (Leuconostoc mesenteroides), Polymyxin (Bacillus polymyxa), Colistin (Bacillus colistrium), Bacitracin (Bacillus licheniformis), L-Glutamic acid (Brevibacterium lactofermentum, Microbacterium ammoniaphilum), and acetone and butanol (Colstridium acetobutylicum, Clostridium saccharoperbutylacetonicum). See generally M. Sanders, Bacteriophages of Industrial Importance, in PHAGE ECOLOGY, 211–44 (S. Goyal, C. Berba and G. Bitton eds. 1987). Thus, the present invention may, for example, be employed in a fermentation process for producing any of the foregoing products with the foregoing bacteria in the manner described herein.

A second aspect of the present invention relates to a bacteriophage resistant, recombinant bacterial cell which contains phage encoded resistance (Per). The mechanism comprises a bacteriophage origin of replication (ori) operatively associated with a DNA sequence incapable of producing live bacteriophage. The bacteriophage ori incorporated into the bacterial cell ultimately competes with the bacteriophage ori contained on intact bacteriophage DNA genome injected into the bacteria upon infection for binding to DNA polymerase.

Once the bacteriophage that is capable of infecting a given bacterial cell is identified and isolated, the bacteriophage ori can be isolated and then cloned into the susceptible bacteria, thereby rendering the bacteria resistant to the bacteriophage. The bacteriophage ori can be identified and isolated in accordance with the method described above, or alternatively, from known bacteriophage DNA libraries prepared with plasmid or phage vectors.

Any bacterial species that is susceptible to infection by a given bacteriophage can be manipulated genetically in accordance with the instant invention to produce bacteriophage resistant recombinant bacteria. Preferred bacteria include those that are capable of fermenting a food substrate, more preferably milk. In another preferred embodiment, the bacterial cell is a lactic acid bacterium; more preferred is a bacteria selected from the lactococci.

Figure 1A:
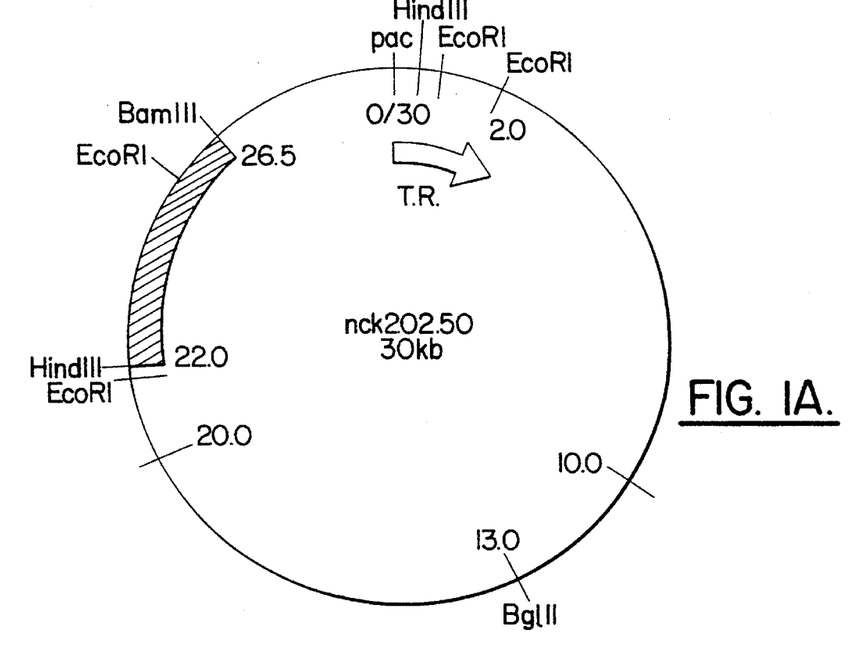
FIGS. 1A and 1B show the restriction endonuclease maps of Phage nck202.50 ($\phi$50), wherein t.r. means terminal redundancy, and pac represents a packaging site. The bacteriophage genome is represented as a circular molecule. Only two of the 13 HindIII sites are shown. The arrow denotes the direction of packaging.
Figure 2A:
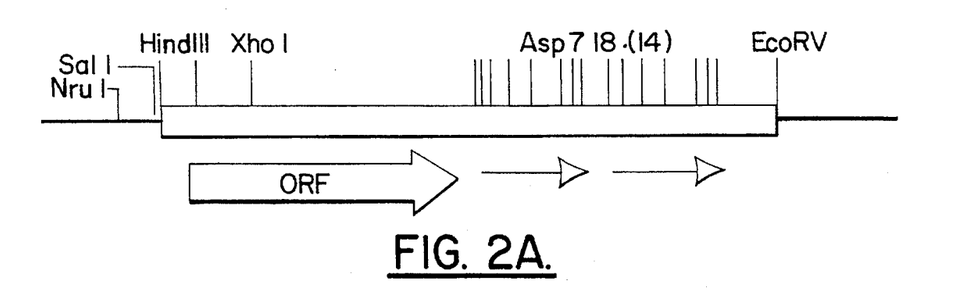
FIG. 2A depicts the physical map of the 1.4-kb insert in pTRK104. The positions of the ORF and direct repeats are indicated.
Figure 2B:
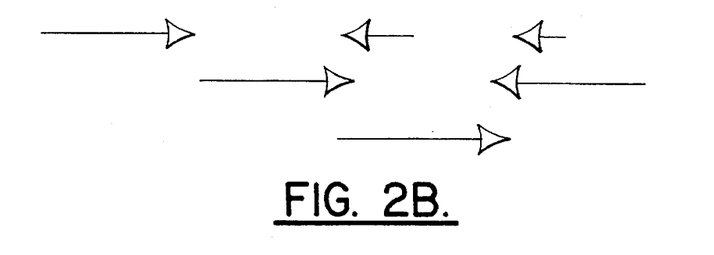
FIG. 2B shows the sequencing strategy for the pTRK104 insert. Only the repeated sequence was determined from both strands.

In another embodiment of the present invention, Per is carried by an extrachromosomal plasmid. The most preferred embodiment in this respect is Lactococcus lactis subsp. lactis NCK298, which has been deposited at the American Type Culture Collection, 12301 Parklawn Drive, Rockville, Md. 20852 USA, in accordance with the provisions of the Budapest Treaty, on Aug. 10, 1990, and given ATCC Accession Number 68379. NCK298 contains plasmids pTRK104 and pTRK2030 (the lattter conjugally introduced). pTRK104, the preparation of which is described in the Examples set forth below, is an E. coli plasmid containing a 1.4-kb region isolated from the genome of bacteriophage nck202.50 ($\phi$50). The genome map of $\phi$50 is shown in FIG. 1A. A physical map of the 1.4-kb insert, which contains Per, is illustrated in FIG. 2A. FIG. 2B illustrates the sequencing strategy for the pTRK104 insert. The 1.4-kb insert contains the ori of $\phi$50, which was found to comprise a 236-bp sequence illustrated in FIG. 3. The sequence and analysis of the insert are described more fully in Example 4 below.

In addition to encoding resistance to bacteriophage $\phi$50 from which it originated, Per is also active against another, genetically distinct bacteriophage ($\phi$48), which is also unaffected by Hsp. Both Per-sensitive bacteriophages were isolated on pTR2030-containing transconjugants and were found to be resistant to the Hsp mechanism encoded by pTR2030. In contrast, Hsp-sensitive bacteriophages, $\phi$31, $\phi$35, $\phi$36, were not affected by Per. Plaquing efficiencies and infective centers for these phages remained at 1.0 on hosts bearing pTRK104. In the case of phages $\phi$48 and $\phi$50, adsorption was not affected, but the numbers of infective centers formed on pTRK104 bearing cells was reduced significantly.

The evidence set forth herein strongly suggests that the Per region is the origin of replication for bacteriophage $\phi$50. First, since the region involved in Per does not direct the expression of a protein, it is probable that the resistance encoded by Per reflects the titration of essential bacteriophage regulatory signals by plasmids containing this region. Second, the Per region can be shown to have a negative impact on the replication of $\phi$50 DNA, whereas there is no effect on the replication of an insensitive bacteriophage, $\phi$31. Third, the presence of the Per region on the plasmid pTRK139 leads to an increase in its replication rate after infection with $\phi$50, though not after infection with $\phi$31. Finally, the Per region itself bears the hallmarks associated with bacteriophage replication origins, repeated and inverted repeats and terminator-like structures. See Bramhill, D. and Kornberg, A. Cell 54:915–918 (1988); Mosig, G., Am. Soc. Microbiol. A.S.M. (1983); Furth, M. E. and Wickner, S. H., Lambda II, Cold Spring Harbor Publications (1983).

As stated above, a successful bacteriophage infection relies upon an interaction between a bacteriophage or host-encoded DNA polymerase and the bacteriophage ori. The presence of the ori on a multicopy plasmid would be expected to interfere with the normal lytic process by titrating DNA polymerase and diverting replication towards the plasmid. This is expected to result in the uncontrolled replication of plasmid DNA. This theory is consistent with the finding that Per of $\phi$50 is effective only against bacteriophage with which it shares homology ($\phi$48) in the region believed to encode the phage origin of replication. Those bacteriophages unaffected by the specific Per sequence disclosed herein differ in that they must utilize an alternative ori sequence and are therefore not susceptible to any titration effects on the bacteriophage-directed DNA polymerase.

The Per phenotype is not a generalized feature of cloned bacteriophage DNA. A randomly selected bacteriophage fragment did not affect the proliferation of $\phi$50, despite a larger region of homology (2.5-kb) to the bacteriophage than that possessed by pTRK104 (1.4-kb) or its derivatives. The possibility of homologous recombination and concomitant disruption of bacteriophage sequences as a cause of Per activity was accordingly ruled out.

Given the similarity of the Per and Hsp phenotypes when both are cloned in the vector pSA3, it appears that both affect similar points in the bacteriophage lytic cycle. However, it is obvious that they are genotypically unrelated. The Hsp essential region has been cloned and sequenced and shown to be a large single gene whereas the Per phenotype is the result of a non-coding region of repeated sequences. The Per region shares homology with both bacteriophages to which it encodes resistance, but the Hsp region does not. See Jarvis, A. W. and Klaenhammer, T. R., Appl. Environ. Microbiol. 51: 1272–1277 (1986). Finally, the Hsp mechanism is slightly heat sensitive in NCK203, whereas Per is not. Nonetheless, it is significant that the Hsp gene product has been shown to interfere with bacteriophage DNA replication. It may be that the Hsp gene product is also ori-specific, but only against the φ31-type ori, and not that of bacteriophages φ48 and φ50.

*L. lactis* strain NCK298, which contains both pTR2030 and pTRK104, is insensitive to contaminating levels of bacteriophages representing both Per-resistant (φ31) and Hsp-resistant (φ50) groups. Thus, Hsp+ and Per+ can work in concert to provide a more extensive range of insensitivity than either mechanism used in isolation.

Plasmid pTRK104 can be easily isolated from *L. lactis* NCK298 by lysing the cells via the procedure of Anderson, D. A., and McKay, L. L., *Appl. Environ. Microbiol.* 46:549–552 (1983). Plasmid pTRK104 can be visualized among the other resident plasmids in NCK298 after electrophoretic migration of the DNA sample in agarose gels; or isolated in pure form by transformation into competent cells of *E. coli* and selectrion for $Cm^r$ transformants via standard protocols. See Hill, c. et al., *Appl. Environ. Microbiol.* 55: 1684–1686.

A third aspect of the present invention relates to a defined bacterial starter culture capable of fermenting a predetermined product. The bacterial starter culture comprises the bacteriophage resistant, recombinant bacteria as described above. That is, the recombinant bacteria contains at least a first bacteriophage defense mechanism, Per, which comprises a bacteriophage origin of replication, ori, operatively associated with a DNA sequence incapable of producing live bacteriophage. The use of the instant bacteriophage resistant bacteria in a starting culture increases the longevity of the culture, the end result being a more economical fermentation process on an industrial scale. Bacterial starter cultures comprising the bacteriophage-resistant transformed bacteria can be used in the fermentation of a variety of products, as described above. A preferred bacterial genus is the lactococci, and preferred species are *L. lactis subsp. lactis* and *L. lactis subsp. cremoris*.

The bacterial starter culture may consist of one bacterial strain, i.e., a pure culture. In this case, substantially all, or at least a significant portion of the bacterial starter culture would generally comprise the transformed bacterial cells. In the alternative, the starter culture may comprise several bacterial strains, i.e., a defined mixed culture, wherein a portion of each bacterial strain is bacteriophage-resistant in accordance with the instant invention. The ideal situation in either case would be to provide starter cultures wherein substantially all the bacterial cells are rendered bacteriophage-resistant.

A fourth aspect of the present invention contemplates a method of conducting a fermentation of a product employing a bacterial starter culture of the instant invention. A fermentation process using the bacteriophage-resistant recombinant bacteria of the present invention may be conducted on a less interrupted basis since the problems of massive bacteriophage infection and subsequent lysis of a predominant portion of the initial bacterial starter culture are alleviated. For example, as explained in Example 6 below, bacteriophage surviving through a $Per^+$ host are incapable of circumventing $Per^+$ in subsequent infections.

The fermentation apparatus and conditions under which fermentation should be conducted may be selected and determined, respectively, by persons of ordinary skill in the art such as to produce the desired product while maintaining the viability of the bacteriophage resistant recombinant bacteria in the starter culture. Reference in this regard is made to the publications above.

A fifth aspect of the present invention relates to a recombinant DNA vector comprising a bacteriophage origin of replication, ori, operatively associated with a DNA sequence incapable of producing live bacteriophage. Any vector capable of transforming a given bacterial host cell can be used in accordance with the present invention. A preferred vector according to the present invention is a plasmid, and more preferred is a plasmid isolated from *E. coli*. In addition, as described the examples below, shuttle vectors may be used since they are capable of replicating stably in two different hosts and thus can move DNA from one organism to another. In a more preferred embodiment of the present invention, the DNA sequence comprising ori is derived from a bacteriophage which is capable of infecting a fermentative bacterium. Bacteria that are capable of fermenting foods, particularly dairy products such as milk, are more preferred, i.e., lactic acid bacteria more particularly, those belonging to the lactococci.

In the most preferred embodiment, the recombinant vector is an *E. coli* plasmid containing the ori of φ50, designated pTRK104, the preparation and analysis of which are set forth in the Examples.

Isolation of bacteriophage resistance mechanisms from lytic bacteriophage genomes such as in the instant invention may provide a wealth of alternative defenses that can be employed to protect industrial strains against failure due to bacteriophage attack. The Per phenotype is not dependent on the production of repressors, nor on the transcription of antisense RNA. Because of this, no energy is expended by the resistant host, other than normal plasmid replication, on maintaining the Per response to bacteriophage attack. In addition, in at least one instance, the Per mechanism was effective against a genetically homologous bacteriophage (φ48) other than the "source bacteriophage" (φ50), which illustrates the potency of Per. Further, two distinct resistance mechanisms, such as $Per^+$ and $Hsp^+$ for example, can work in concert to provide a more extensive range of bacteriophage resistance than any sole resistance mechanism.

The examples which follow are illustrative of specific embodiments of the invention, and various uses thereof. They are set forth for explanatory purposes only, and are not to be taken as limiting the invention.

EXAMPLES

The bacterial strains used in the examples below are presented in Table 1. *L. lactis* strains were propagated at 30° C. in M17 broth as described in Terzhagi, B.E. et al., *Appl. Environ. Microbiol.* 29:807–813 (1975), or in M17 broth with 0.5% glucose substituted for lactose (M17G) when appropriate. Bacteriophages were propagated and titrated as described in Klaenhammer, T. R. et al., *J. Gen. Microbiol.* 131:1531–1541 (1985). *Escherichia coli* strains were grown in LB broth at 37° C. with shaking. See Silhavy, T. J. et al., "Experiments With Gene Fusions", Cold Spring Harbor, N.Y. (1984) When required for selection, the following antibiotics were added at the indicated concentrations in micrograms per milliliter: for *E. coli*, ampicillin, 50; chloramphenicol, 20; for lactococci, erythromycin, 5. Solid surface conjugal matings and selection of $Lac^+$ transconjugants were performed as described in Klaenhammer, T. R. et al., *J. Gen. Microbiol.* 131:1531–1541 (1985) and McKay, L. L. et al., *Appl. Environ. Mircobiol.* 40:68–74 (1980). Protoplasts of *L. lactis* NCK203 were transformed as described in Kondo, J. K. et al., *Appl. Environ. Microbiol.* 43:1213–1215 (1982), with some modifications. See Hill, C. D. et al., *Appl. Environ. Microbiol.* 55:1684–1689 (1989). Transformants were selected on 1.5μg erythromycin per ml.

Bacteriophage adsorption assays were conducted as described in Sanders, M.E. et al., *Appl. Environ. Microbiol.* 46:1125–1133 (1983). Center of Infection (COI) data were calculated as described in Klaenhammer, T. R. et al., *J. Gen. Microbiol.*, 131:1531–1541 (1985). Growth curves were performed as follows; 10 ml of M17G, 50 μl of 1M $CaCl_2$, and 200μl of an overnight culture, were added to a sterile cuvette and the $OD_{600}$ was monitored with time. After 1 hr, bacteriophage were added to a final level of $10^6$ plaque forming unites per ml.

Plasmid isolation, restriction, ligation and transformation in *E. coli* DH1 was performed as described in Maniatis, T. E. et al., *Molecular Cloning,* Cold Spring Harbor Laboratory, Cold Spring Harbor, N.Y. (1982). Lactococcal bacteriophage DNA was isolated as previously described. See Jarvis, A. W. and T. R. Klaenhammer, *Appl. Environ. Microbiol.* 51: 1272–1277 (1986).

Nucleotide sequences of both strands were determined by the dideoxy chain termination method set forth in Sanger, F. S. et al., *Pro. Nat'l. Acad. Sci.* (USA) 74:5463–5467 (1977) and the Sequenase enzyme (Stratagene) using either the recombinant M13 single stranded templates or pBluescript clones. Synthetic oligonucleotide primers (17-mers) were synthesized in those instances when a subclone was too large to be fully sequenced from commercially available primers.

Bacteriophage φ50 replication was analyzed as follows. Sensitive or resistant cells were freshly grown to an optical density of 0.5 at 600 nm. $CaCl_2$ to a final concentration of 10 mM, was added, followed by the addition of the test bacteriophage strain at a multiplicity of infection (MOI) greater than 1.0. Infected cells were incubated at 30° C. At various time points, 1 ml of cells was harvested in an eppendorf centrifuge, and the pellet was frozen rapidly by immersion in ultra-cold ethanol (−70° C.). After thawing on ice, the pellet was resuspended in 400 μl of ice-cold lysis solution (6.7% sucrose, 50 mM Tris, 1 mM EDTA, pH 8.0). Lysozyme (20 μl of a 10 mg/ml stock solution) was added and incubation on ice was continued for 20 min. Sodium dodecyl sulfate (50 μl of a 10% stock) was added. Proteinase K (20μl of a 20 mg/ml stock) was then added and the lysate incubated at 65° C. for 20 min. The resulting clear suspension was extracted once with TE-saturated phenol, followed by a chloroform:isoamyl-alcohol (24:1) extraction. One-tenth volume of 3M sodium acetate and two volumes of cold 95% ethanol were added to precipitate the total DNA. The DNA pellet was finally resuspended in 100 μl $dH_2O$. 5 μl were generally sufficient for restriction analysis.

Unless indicated otherwise, all percents are by weight.

TABLE 1

| | Bacterial Strains and Plasmids | |
|---|---|---|
| Strain or Plasmid | Relevant Characteristics | Source or derivation |
| *L. lactis* | | |
| NCK202 | str15, host for φ50, φ48, φ31 | Hill et al., 1989b |
| NCK203 | $R^-/M^-$ derivative of NCK202 | Hill et al., 1989b |
| NCK204 | NCK203, pTR2030, Hsp+, R+/M+ | Hill et al., 1989b |
| NCK213 | NCK203, pTRK103, Per+ | Transformant, this study |
| NCK214 | NCK203, pTRK104, Per+ | Transformant, this study |
| NCK215 | NCK203, pSA3 | Transformant, this study |
| NCK216 | NCK203, pTRK106 | Transformant, this study |
| NCK298 | NCK203, pTR2030, pTRK104, pTR140, Lac+, Hsp+, $R^+/M^+$, Per+ | Transconjugant, this study |
| NCK294 | NCK203, pTRK136, Per+ | Transformant, this study |
| NCK295 | NCK203, pTRK137, Per− | Transformant, this study |
| NCK296 | NCK203, pTRK138, Per+ | Transformant, this study |
| *E. coli* DH1 | Transformation host | Hanahan, 1983 |
| Plasmids | | |
| pBluescript | Cloning vector, $Ap^r$ | Stratagene, La Jolla, CA. |
| pSA3 | Shuttle vector, $Cm^r$, $Em^r$, $Tc^r$ | Dao and Ferretti, 1985 |
| pSA34 | ori selection vector, $Cm^r$, $Em^r$, $Tc^r$ | Sanders and Schultz, 1989 |
| pTRK102 | $Ap^r$ | pBluescript::4.5-kb φ50 fragment |
| pTRK103 | $Cm^r$, $Em^r$, Per+ | pSA3::4.5-kb φ50 fragment |
| pTRK104 | $Cm^r$, $Em^r$, Per+ | EcoRV deletion of pTRK103 |
| pTRK105 | $Ap^r$ | pBluescript::2.5-kb φ50 fragment |
| pTRK106 | $Cm^r$, $Em^r$, Per− | pSA3::2.5-kb φ50 fragment |
| pTRK136 | $Cm^r$, $Em^r$, Per+ | pTRK104, opposite orientation |
| pTRK137 | $Cm^r$, $Em^r$, Per− | pTRK104, Asp718 deletion |
| pTRK138 | $Cm^r$, $Em^r$, Per+ | pTRK104, SalI-XhoI deletion |
| pTRK141 | $Cm^r$, $Em^r$ | pSA34::4.5-kb φ50 fragment |
| pTR2030 | Hsp+, Tra+, $R^+/M^+$ | Klaenhammer and Sanozky, 1985 |

EXAMPLE 1

Cloning of per gene from Phage nck202.50

Figure 1B:
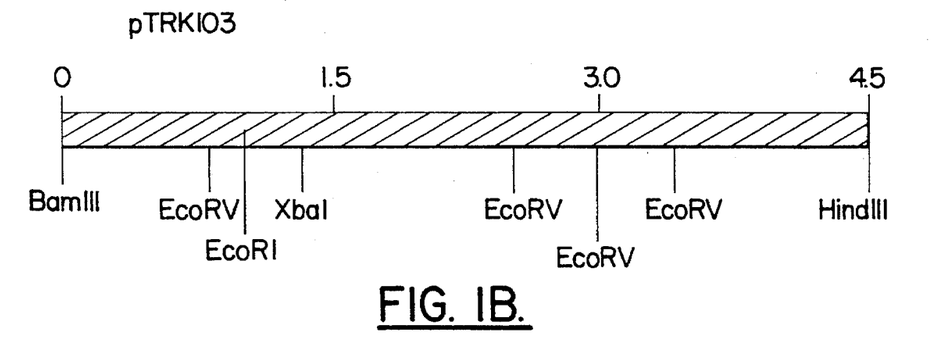

This example describes the isolation and characterization of a gene encoding bacterophage encoded resistance. Phage nck202.50, designated φ50, is a 29.8-kb virulent small isometric-headed bacteriophage. It possesses a unique BamH1 site in addition to at least 13 HindIII sites which have not been mapped on the bacteriophage genome, as shown in FIG. 1A. To isolate Per, bacteriophage φ50 DNA was digested with BamH1 and HindIII and shotgun cloned into similarly digested pBluescript. Recombinant plasmids containing both possible BamH1—HindIII inserts were recovered from transformants. The 4.5-kb insert from one of the plasmids, pTRK102, was subcloned as a BamH1—SalI fragment in the streptococcal *E. coli* shuttle plasmid pSA3 in accordance with the method described in Dao, M.L. et al., *Appl. Environ. Microbiol.* 49:115–119 (1985), to create pTRK103, illustrated in FIG. 1B. pTRK103 was introduced to *L. lactis* NCK203 via protoplast transformation. NCK203 is a derivative of NCK202 which has been cured of a native R/M plasmid pTRK68. See Hill, C. K. et al., *Appl. Environ. Microbiol.*, 55:2416–2419 (1989). One NCK203 transformant, NCK213, was verified as possessing intact pTRK103 by plasmid profile analysis. The plasmid was isolated from NCK213 and retransformed to E. coli DH1 and subjected to restriction enzyme analysis. No rearrangements in pTRK103 were detected (data not shown).

EXAMPLE 2

Identification of pTRK103 as Per+

The effect of pTRK103 on φ50 was investigated using standard plaque assays. When present in NCK203, pTRK103 strongly inhibited the ability of φ50 to form plaques. Plaques were pinpoint in size and difficult to enumerate; the EOP was estimated at 0.35. See Table 2. When present on NCK203 harboring the shuttle vector pSA3 without an insert, φ50 gave normal plaques of 1.6 mm in diameter and an EOP of 1.0 (Table 2). NCK203 (pTRK103) also inhibited plaque formation by the small isometric headed bacteriophage φ48. The plaque size was reduced and an EOP of 0.5 was estimated for this bacteriophage (Table 2). However, NCK203 (pTRK103) did not inhibit plaque formation by the small isometric-headed bacteriophages φ31, φ35 or φ36 (data for φ31 in Table 2, others not shown). pTRK103 was introduced into L. lactis MG1363 by protoplast transformation and one transformant, NCK219, was challenged with three bacteriophages lytic for that host. The presence of pTRK103 did not affect the plaque size or EOP of the prolate bacteriophage φc2, or the small isometric bacteriophages φp2 or φsk1. Conversely, the Hsp+ plasmid pTK6 retarded normal plaque formation for φc2, φp2 and φsk1 in MG1363. See Hill, C. et al. *Appl. Environ. Microbiol.*, 55:1684–1689 (1989). pTK6 also retarded normal plaque formation for φ31, φ35 and φ36 in NCK203. See, Hill, C. et al., *Appl. Environ. Microbiol.* 55:2416–2419 (1989). The Hsp+ activity directed by pTK6 did not inhibit either φ48 or φ50 in the NCK203 background.

A second clone was constructed to evaluate the possibility that the resistance encoded by pTRK103 is a general phenomenon of bacteriophage fragments distributed around the φ50 genome. Bacteriophage φ50 DNA was digested with HindIII and shotgun cloned into HindIII-digested pBluescript. A bank of clones with inserts representing the bacteriophage genome was obtained. One recombinant plasmid, pTRK105, which contained an insert of approximately 2.5-kb was randomly selected, and the insert was subcloned in pSA3 as a BamH1—Xba1 fragment. The resultant recombinant plasmid, pTRK106, was introduced to NCK203 by protoplast transformation. The pTRK106 transformant was challenged with φ48 and φ50. This randomly selected bacteriophage fragment had no effect on the plaque size or the efficiency of plaguing of either bacteriophage. See Table 2.

TABLE 2

Bacteriophage nck202.50 (φ50), nck202.48 (φ48), and nck202.31 (φ31) reactions on L. lactis NCK203 and derivatives

| PHAGE | HOST (PLASMID) | EOP | PLAQUE SIZE/mm |
|---|---|---|---|
| φ50 | NCK203 | 1.0 | 1.6 |
| φ50 | NCK215 (pSA3) | 1.0 | 1.6 |
| φ50 | NCK213 (pTRK103) | 0.35 | 0.2 |
| φ48 | NCK203 | 1.0 | 1.5 |
| φ48 | NCK213 (pTRK103) | 0.5 | 0.2 |
| φ31 | NCK203 | 1.0 | 1.5 |
| φ31 | NCK213 (pTRK103) | 1.0 | 1.5 |
| φ50 | NCK216 (pTRK106) | 1.0 | 1.6 |
| φ48 | NCK216 (pTRK106) | 1.0 | 1.5 |
| φ50 | NCK214 (pTRK104) | 0.42 | 0.2 |
| φ48 | NCK214 (pTRK104) | 0.5 | 0.2 |
| φ50 | NCK298 (pTR2030, pTRK104) | 0.44 | 0.2 |
| φ31 | NCK298 (pTR2030, pTRK104) | $<10^{-8}$ | no plaques |

EXAMPLE 3

Figure 1C:
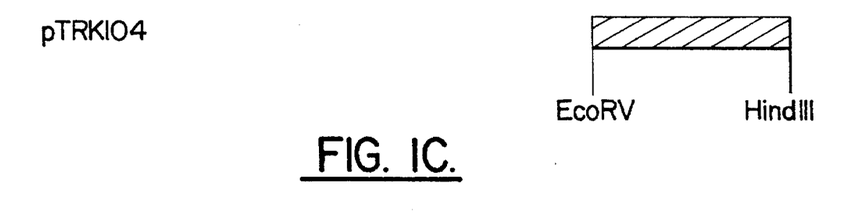
FIG. 1C shows the 1.4-kb EcoRV—HindIII fragment thereof.

Subcloning the Per Region pTRK103 contains four EcoRV sites, three of which are internal to the 450 insert. See FIG. 1B. pTRK103 was digested with EcoRV, religated and transformed to E. coli DH1. Cm$^r$-transformants were recovered containing plasmids which had been deleted of one or more of the EcoRV fragments. These plasmids were transformed to NCK203 and examined for their effect on φ48 and φ50. All derivatives directed the same Per+ resistance phenotype as did pTRK103. This localized the resistance determinant to a 1.4-kb EcoRV—HindIII fragment which remained undisturbed in all the in vitro deletions. See FIG. 1C. This fragment was present in all deletion derivatives because there is no EcoRV site to the right-hand side of this region. The Per+ phenotype against φ48 and φ50 (Table 2) is encoded by a plasmid containing only this 1.4-kb region, pTRK104, illustrated in FIG. 2A. The 1.4-kb insert in pTRK104 was inverted by digesting the plasmid with EcoRV and Nru1, which cut on either side of the insert (FIG. 2A). After religation, a recombinant plasmid was recovered, pTRK136, in which the insert was present in the opposite orientation. pTRK136 directed Per+ at an identical level to pTRK104, indicating that any information necessary for Per activity is located within the fragment.

EXAMPLE 4

Sequence and Analysis of Per

Figure 4A:
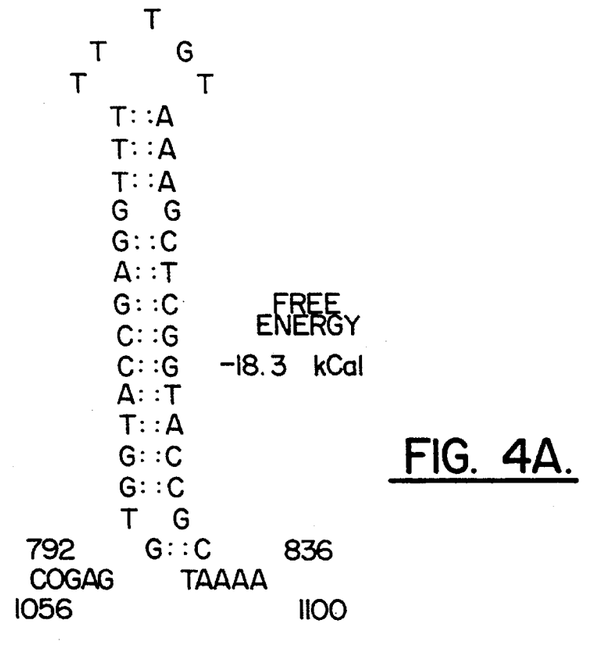
FIGS. 4A and 4B shows the large direct repeats having contained therein inverted repeats shown as hairpin loops. The positions of the inverted repeats are also indicated.
Figure 4B:
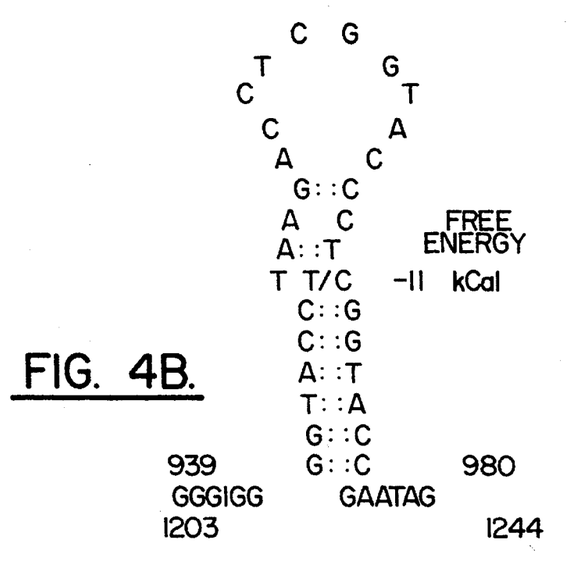

The 1.4-kb insert in pTRK104 was subcloned in M13mp18 and mp19 as an EcoRV—Cla1 fragment and sequenced by the strategy illustrated in FIGS. 2A and 2B. Sequence analysis revealed a single open reading frame (ORF) of 701-bp. See FIG. 3. An unexpected result was the presence of a second HindIII site 69-bp from the pSA3-derived HindIII site used in the original cloning protocol. This small fragment was either inserted fortuitously during the ligation reaction, or is a contiguous φ50 fragment which was included as a result of a partial digestion. This region includes the potential start codon for the 701-bp ORF contained within the fragment. The 3' end of the insert proved difficult to sequence, and was resolved finally by conducting the polymerase reactions at 0° C., a recommended procedure for regions rich in secondary structure. The resulting unambiguous sequence revealed a direct repeat of 236-bp separated by 28-bp (FIG. 3). This extremely large direct repeat was almost 99% identical, with only 3 mismatches in the 236-bp repeat. Detected within the direct repeat were a number of inverted repeats capable of forming stable stem-loop structures. See FIGS. 4A and 4B. These stable structures are typical of sequences associated with rho-independent termination. The 10-bp sequence, GGTACCGAGG, was also repeated four times within each larger direct repeat (FIG. 3). In addition, the palindromic sequence GGATCC was repeated 14 times overall in this 500-bp region.

EXAMPLE 5

Recognition of Repeated Sequences Responsible for Per Activity pTRK104 was digested with Sal1 and Xho1 and religated. The resulting construct, pTRK138, no longer possessed the putative start codon for the ORF. pTRK138 was reintroduced into L. lactis NCK203 and challenged with φ50 and φ48. The Per$^+$ phenotype was observed (data not shown), indicating that the ORF is not involved in the bacteriophage resistance phenotype. A second derivative was constructed to assess the effect of the repeated sequence on the Per phenotype. The palindromic repeat GGATCC, present 14 times within the repeated regions, is the recognition site for the type II restriction endonuclease Asp718 and its isoschizomer Kpn1. pTRK104 was digested with Asp718 and religated to form pTRK137. This plasmid lost approximately 400-bp, including most of the large direct and inverted repeats present in pTRK104. When introduced into NCK203, pTRK137 did not direct any resistance against either bacteriophage φ48 or φ50, from which it was concluded that the repeated sequence is essential for the Per$^+$ phenotype.

EXAMPLE 6

Effect of pTRK104 on φ50

Figure 5A:
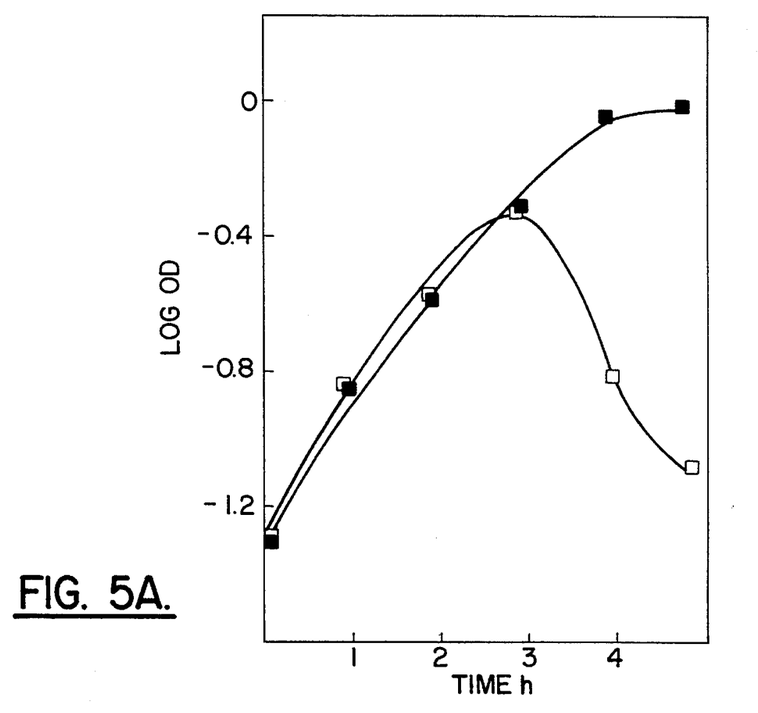
FIG. 5A shows effect of lytic bacteriophage $\phi$50 on the growth of NCK215 (pSA3) (open boxes) and NCK214 (pTRK104) (filled boxes).

The growth of NCK203 containing pTRK104, i.e., NCK214, at 30° C. in the presence and absence of φ50 was examined. See FIG. 5A. NCK214 grew normally in the presence of φ50 at an initial bacteriophage level of $1 \times 10^4$ per ml. In comparison, the control strain NCK215, containing the cloning vector pSA3, was rapidly lysed under the same conditions. The mechanism of action of Per was examiner further by conducting bacteriophage adsorption and center of infection (COI) studies on NCK214. Adsorption studies were performed at 30° C. on NCK203 derivatives harboring either pSA3 (NCK215) or pTRK104 (NCK214). NCK214 adsorbed φ50 at 87%, compared with 84% for the sensitive host, NCK215. However, the number of infectire centers formed on NCK214 was 43% of that formed on NCK215. Standard plaque assays conducted at high temperature (39° C.) revealed that Per is not heat sensitive. Similar plaque sizes and EOP were obtained at both 39° C. and at 30° C. (data not shown). Bacteriophage were inhibited to the same extent by pTRK104 regardless of whether or not the bacteriophage was first propagated on a host bearing pTRK104. Therefore bacteriophage surviving through a Per$^+$ host are incapable of circumventing Per in subsequent infections.

EXAMPLE 7

Per$^+$ Affects Bacteriophage DNA Replication

The internal replication of φ50 DNA was followed using a rapid DNA isolation procedure in which bacteriophage-infected cells were harvested at various times and examined for bacteriophage DNA. Forty minutes after bacteriophage infection, the appearance of φ50 DNA could be clearly detected in the propagating host, NCK203. Bacteriophage directed replication of the φ50 genome prior to cell lysis was reflected in the accumulation of φ50-specific DNA fragments. With increasing time after infection, bacteriophage DNA became more evident, suggesting continued replication. In the NCK203 derivative containing pTRK138, NCK296 (Per$^+$), bacteriophage DNA replication over the identical time course was less pronounced suggesting that Per interferes with bacteriophage DNA replication. It is significant that the plasmid bearing Per, pTRK138, increased in copy number after infection. An increase in the copy number of pTRK138 was not apparent during φ31 infection of NCK296, nor was there any decrease in φ31 DNA replication. Thus, a plasmid bearing the bacteriophage replication ori should increase in copy number as a consequence of bacteriophage infection. It is noteworthy that the increased amount of pTRK138 evident in the φ50-infected NCK296 was not present in a covalently closed circular (CCC) form. Uncut DNA preparations did not show increased amounts of the CCC plasmid, suggesting that pTRK138 is amplified as a concatemeric form during bacteriophage infection (data not shown). These data indicate that the Per region is the bacteriophage origin, or one of the bacteriophage origins of replication (ori).

The pSA3 cloning vector, contained in NCK215, was not amplified after bacteriophage φ50 infection. Therefore, the presence of the repeated φ50 DNA sequence is required for amplification of pTRK138. The 4.5-kb insert from φ50, contained in pTRK103, was subcloned to the pSA3 derivative pSA34, a derivative of pSA3 which has been deleted of the gram-positive origin of replication. See Sanders, M.E. et al., Eur. Pat. App. 88/118362.8. L. lactis NCK203 could not be transformed with the resulting construct, pTRK141. Thus, it was concluded that the putative bacteriophage φ50 ori is incapable of supporting viable plasmid replication in the absence of a concurrent bacteriophage infection.

EXAMPLE 8

Figure 5B:
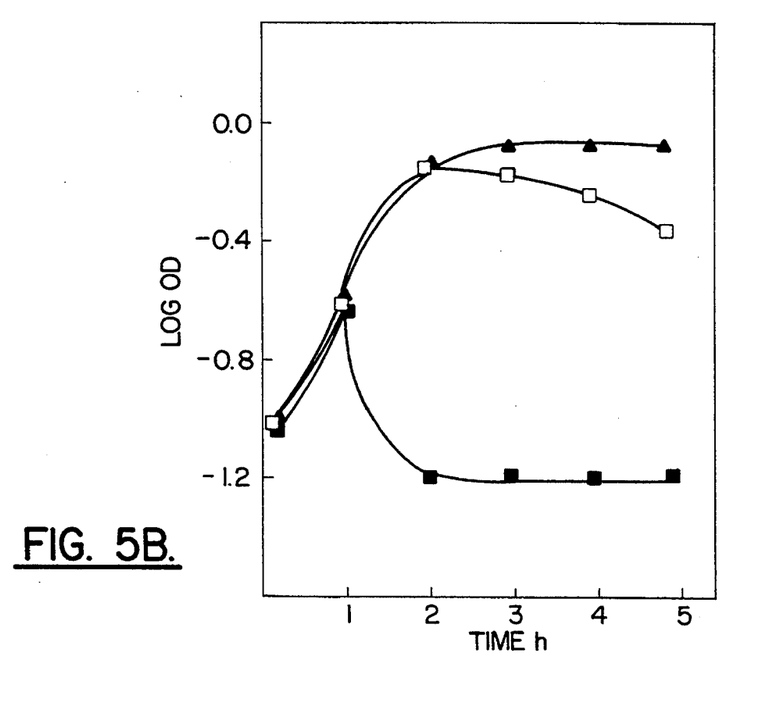
FIG. 5B shows the effect of lytic bacteriophages $\phi$31 and $\phi$50, together, on the growth of NCK214 (filled boxes), NCK204 (pTR2030) (open boxes), and NCK298 (pTR2030, pTRK104) (filled triangles).

Combining HSp$^+$ and Per$^+$ in NCK203 pTR2030 was introduced to NCK214 (pTRK104) by solid surface conjugation with a donor strain NCK1. Transconjugants were selected initially for acquisition of the Lac$^+$ phenotype encoded by the non-conjugative plasmid pTR1040. Lac$^+$ (pTR1040) Em$^r$ (pTRK104) transconjugants were subsequently screened for the presence of pTR2030. One transconjugant, NCK298, containing both pTR2030 and pTRK104, was selected and examined for combined resistance to bacteriophages φ50 and φ31, insensitive to Hsp$^+$ and Per$^+$, respectively. NCK298 is completely resistant to φ31 in standard plaque assays, a typical reaction for this bacteriophage on pTR2030-bearing hosts. The host bearing both plasmids also displayed the typical Per$^+$ response against φ50 (Table 2). Growth of NCK298 was not affected when both φ50 and φ31 were present at initial levels of $10^6$ pfu/ml. See FIG. 5B. Strains containing either pTR2030 or pTRK104 were inhibited by the presence of both types of bacteriophage. These data indicate that both resistance mechanisms can operate simultaneously in the NCK203 background and expand the bacteriophage resistance of this strain.

The foregoing examples are illustrative of the present invention, and are not to be construed as limiting thereof. The invention is defined by the following claims, with equivalents of the claims to be included therein.

That which is claimed is:

1. A method of imparting bacteriophage resistance to lactococcal bacteria contained in a fermentative culture medium, comprising:

(a) conducting a fermentation of a milk substrate in a medium containing a defined bacterial culture including at least one lactococcal bacteria until bacteriophage are detected in the medium, said bacteriophage being specific to at least one lactococcal bacteria in said medium;

(b) isolating said bacteriophage;

(c) digesting DNA of the bacteriophage to produce a library of DNA fragments;

(d) transforming said one lactococcal bacteria susceptible to said bacteriophage with said library of DNA fragments to provide transformed lactococcal bacteria by ligating said DNA fragments to a replicating plasmid vector and transforming said one bacteria susceptible to said bacteriophage with said vector;

(e) selecting from among the transformed lactococcal bacteria a bacteriophage-resistant recombinant lactococcal bacteria;

(f) adding a predetermined amount of said bacteriophage-resistant recombinant lactococcal bacteria to the medium; and (g) commencing fermentation of said substrate in said medium with said bacteriophage-resistant recombinant lactococcal bacteria.

2. The method of claim 1, wherein the defined bacterial culture is a pure culture.

3. The method of claim 1, wherein the defined bacterial culture is a mixed culture.

4. A lactococcal bacterial cell containing a bacteriophage defense mechanism, said defense mechanism comprising a lactococcal phage origin of replication (ori) which is a substrate for DNA polymerase and which is operatively associated with a DNA sequence which does not encode live lactococcal phage, wherein said lactococcal bacterial cell is susceptible to infection by a lactococcal phage, and wherein the DNA of said lactococcal phage, once injected into said bacterial cell, competes with said bacteriophage defense mechanism for binding to DNA polymerase; and wherein said DNA polymerase is a lactococcal phage DNA polymerase or a lactococcal bacterial DNA polymerase.

5. A bacterial cell of claim 4, wherein said ori and said operatively associated DNA sequence are carried by an extrachromosomal plasmid.

6. A bacterial cell of claim 5, wherein said extrachromosomal plasmid is pTRK104.

7. A defined bacterial starter culture useful for fermenting a product, comprising: a plurality of lactococcal bacterial cells, each containing a lactococcal phage defense mechanism, said lactococcal phage defense mechanism comprising a lactococcal phage origin of replication (ori) which is a substrate for DNA polymerase and which is operatively associated with a DNA sequence which does not encode live lactococcal phage, wherein said lactococcal bacterial cells are susceptible to infection by a lactococcal phage, and wherein the DNA of said lactococcal phage, once injected into said bacterial cell, competes with said phage defense mechanism for binding to DNA polymerase; and wherein said DNA polymerase is a lactococcal phage DNA polymerase or a lactococcal bacterial DNA polymerase.

8. A defined bacterial starter culture of claim 7, which is a pure culture.

9. A defined bacterial starter culture of claim 7, which is useful for fermenting milk.

10. A recombinant DNA vector comprising a lactococcal phage origin of replication (ori) which is a substrate for DNA polymerase and which is operatively associated with a DNA sequence which does not encode live lactococcal phage; and wherein said DNA polymerase is a lactococcal phage DNA polymerase or a lactococcal bacterial DNA polymerase, and said vector is plasmid PTRK104.

11. A method of imparting resistance to bacteriophage nck202.50 to lactococcal bacteria contained in a fermentative culture medium, comprising:

(a) conducting a fermentation of a milk substrate in a medium containing a defined bacterial culture including at least one lactococcal bacteria until bacteriophage nck202.50 is detected in the medium;

(b) isolating said bacteriophage;

(c) digesting DNA of the bacteriophage to produce a library of DNA fragments;

(d) transforming said one lactococcal bacteria susceptible to said bacteriophage with said library of DNA fragments to provide transformed lactococcal bacteria by ligating said DNA fragments to a replicating plasmid vector and transforming said one bacteria susceptible to said bacteria with said vector;

(e) selecting from among the transformed lactococcal bacteria a bacteriophage-resistant recombinant lactococcal bacteria resistant to bacteriophage nck202.50;

(f) adding a predetermined amount of said bacteriophage-resistant recombinant lactococcal bacteria to the medium; and (g) commencing fermentation of said substrate in said medium with said bacteriophage-resistant recombinant lactococcal bacteria.

12. A method according to claim 11, wherein said lactococcal bacteria is *Lactococcus lactis*.

13. A method according to claim 12, wherein said selecting step comprises selecting from among the transformed bacteria a bacteriophage-resistant recombinant bacteria containing plasmid pTRK104.

* * * * *